United States Patent [19]

Bailey et al.

[11] 4,017,522

[45] Apr. 12, 1977

[54] N-(FUROYLOXYETHYL) FATTY ACID AMIDES

[75] Inventors: August V. Bailey; Gordon J. Boudreaux; Gene Sumrell, all of New Orleans; Arthur F. Novak, Baton Rouge, all of La.

[73] Assignee: The United States of America as represented by the Secretary of Agriculture, Washington, D.C.

[22] Filed: Mar. 15, 1976

[21] Appl. No.: 667,063

[52] U.S. Cl. .......................... 260/347.5; 260/404; 260/482 R; 424/285; 424/308; 424/312
[51] Int. Cl.$^2$ ...................................... C07D 307/68
[58] Field of Search ................................ 260/347.5

[56] References Cited

UNITED STATES PATENTS 3,403,126   9/1968   Mod et al. ..................... 260/30.4

*Primary Examiner*—Henry R. Jiles
*Assistant Examiner*—Bernard Dentz
*Attorney, Agent, or Firm*—M. Howard Silverstein; Salvador J. Cangemi; David G. McConnell

[57] ABSTRACT

New ester-amides containing one or more long chain fatty acyl groupings are described which have antimicrobial activity against several pathogenic microorganisms, and have properties making them useful as antimicrobial agents.

6 Claims, No Drawings

N-(FUROYLOXYETHYL) FATTY ACID AMIDES

This invention relates to certain new nitrogen-containing organic compounds. More particularly this invention relates to ester-amides which exhibit antimicrobial activity, and in which at least one of the acyl groupings in the molecule is aliphatic. The ester-amides that are the subject of this invention are characterized by the fact that as growth inhibitors, they are effective against a variety of microorganisms that includes bacteria, yeasts and molds. Some of these ester-amides exhibit broad antimicrobial spectrum, whereas other exhibit selective antimicrobial spectrum.

The compounds which are the subject of this invention are:

N,N-bis(2-benzoyloxyethyl)lauramide,
$[C_6H_5COOCH_2CH_2]_2NCOC_{11}H_{23}$
N,N-bis(2-furoyloxyethyl)lauramide,
$[C_4H_3OCOOCH_2CH_2]_2NCOC_{11}H_{23}$
N,N-bis(2-trimethylacetoxyethyl)lauramide,
$[(CH_3)_3CCOOCH_2CH_2]_2NCOC_{11}H_{23}$
N,N-bis(2-lauroyloxyethyl)benzamide,
$[C_{11}H_{23}COOCH_2CH_2]_2NCOC_6H_5$
N,N-bis(2-oleoyloxyethyl)benzamide,
$[C_{17}H_{33}COOCH_2CH_2]_2NCOC_6H_5$
N,N-bis(2-erucoyloxyethyl)benzamide,
$[C_{21}H_{41}COOCH_2CH_2]_2NCOC_6H_5$
N,N-bis(2-furoyloxyethyl)oleamide,
$[C_4H_3OCOOCH_2CH_2]_2NCOC_{17}H_{33}$
N,N-bis(2-trimethylacetoxyethyl)oleamide,
$[(CH_3)_3CCOOCH_2CH_2]_2NCOC_{17}H_{33}$
N-methyl-N-(2-benzoyloxyethyl)lauramide,
$C_6H_5COOCH_2CH_2N(CH_3)COC_{11}H_{23}$
N-methyl-N-(2-furoyloxyethyl)lauramide.
$C_4H_3OCOOCH_2CH_2N(CH_3)COC_{11}H_{23}$
N-methyl-N-(2-p-toluoyloxyethyl)lauramide,
$CH_3C_6H_4COOCH_2CH_2N(CH_3)COC_{11}H_{23}$
N-methyl-N-(2-trimethylacetoxyethyl)lauramide,
$(CH_3)_3CCOOCH_2CH_2N(CH_3)COC_{11}H_{23}$
N-methyl-N-(2-benzoyloxyethyl)oleamide,
$C_6H_5COOCH_2CH_2N(CH_3)COC_{17}H_{33}$
N-methyl-N-(2-furoyloxyethyl)oleamide,
$C_4H_3OCOOCH_2CH_2N(CH_3)COC_{17}H_{33}$
N-methyl-N-(2-p-toluoyloxyethyl)oleamide,
$CH_3C_6H_4COOCH_2CH_2N(CH_3)COC_{17}H_{33}$
N-methyl-N-(2-trimethylacetoxylethyl)oleamide,
$(CH_3)_3CCOOCH_2CH_2N(CH_3)COC_{17}H_{33}$
N-methyl-N-(2-benzoyloxyethyl)erucamide,
$C_6H_5COOCH_2CH_2N(CH_3)COC_{21}H_{41}$
N-methyl-N-(2-furoyloxyethyl)erucamide,
$C_4H_3OCOOCH_2CH_2N(CH_3)COC_{21}H_{41}$
N-methyl-N-(2-p-toluoyloxyethyl)erucamide,
$CH_3C_6H_4COOCH_2CH_2N(CH_3)COC_{21}H_{41}$
N-methyl-N-(2-benzoyloxyethyl)palmitamide,
$C_6H_5COOCH_2CH_2N(CH_3)COC_{15}H_{31}$
N-methyl-N-(2-furoyloxyethyl)palmitamide,
$C_4H_3OCOOCH_2CH_2N(CH_3)COC_{15}H_{31}$
N-methyl-N-(2-lauroyloxyethyl)benzamide,
$C_{11}H_{23}COOCH_2CH_2N(CH_3)COC_6H_5$
N-methyl-N-(2-palmitoyloxyethyl)benzamide,
$C_{15}H_{31}COOCH_2CH_2N(CH_3)COC_6H_5$
N-methyl-N-(2-oleoyloxyethyl)benzamide,
$C_{17}H_{33}COOCH_2CH_2N(CH_3)COC_6H_5$
N-methyl-N-(2-lauroyloxyethyl)-p-toluamide.
$C_{11}H_{23}COOCH_2CH_2N(CH_3)COC_6H_4CH_3$
N-methyl-N-(2-oleoyloxyethyl)-p-toluamide,
$C_{17}H_{33}COOCH_2CH_2N(CH_3)COC_6H_4CH_3$ The new ester amides which are the subject of this invention were prepared by conventional methods.

The bioactivity of these new nitrogen-containing compounds has been established in vitro but, as will be apparent to those skilled in the arts pertaining to the growth inhibition of bacteria, yeast, and molds, the compounds, besides being used as such, will for utilitarian purposes commonly be formulated using a diluent that can be either liquid, viscous, or solid.

A wide variety of extending agents is operable, the only significant requirement being that the diluent or extender be inert with respect to the ester-amide involved. Petroleum jellies, various alcohols and polyols, vegetable oils and the like are suitable.

In the case of intended use as fungicide in the protective coating composition art, the compounds that are the subject of this invention are compatible with conventional and with drying oil modified alkyds, for example. These new compounds are compatible with various resins, such as polyvinyl chloride, for example, and can serve as both plasticizer and antifungal agent for such materials.

Specific examples showing the preparation of each of the new compounds being claimed are set forth below along with appropriate data in tabular form which is being submitted for the purpose of establishing the growth inhibiting properties of the claimed compounds.

The microorganisms used were obtained from stock cultures. Difco Dehydrated Mycological Agar at pH 7.0 was used to test the inhibition of the test organisms by the compounds.

The ester-amides were screened for their antimicrobial activity against two bacteria — a gram-positive, *staphylococcus aureus*, and a gram-negative, *Escherichia coli*; a yeast, *Torula sp.*; and three molds, *Aspergillus sp.*, *Candida albicans* and *Aspergillus flavus*.

Seeded agar plates were used to measure the antimicrobial activity against bacteria and the yeast. Poured agar plates were used to measure the antimicrobial activity against the molds. The poured agar plates were prepared by pouring dilutions of mold spores over the hardened agar plates.

Filter paper discs 6.5 mm in diameter, made from Whatman Number 1 filter paper were wetted until they were completely saturated with the compounds being tested, and the wetted discs were placed on the surface of the agar plates inoculated with the test organisms.

To eliminate any errors which could result from an insufficient number of tests, a minimum of three experiments, at different times, employing duplicate plates were made for each compound under test.

All test plates were incubated at the optimum growing temperature for each organism and readings were taken after 24, 48, 72 and 120 hr. periods. The results are tabulated in Table I.

TABLE I

The Antimicrobial Activity of Some Fatty Ester-Amides

| Compound | Antimicrobial Activity[a] | | | | | |
|---|---|---|---|---|---|---|
| | Staphylococcus aureus | Escherichia coli | Aspergillus Sp. | Torula Sp. | Candida albicans | Aspergillus flavus |
| 1. N,N-bis(2-benzoyloxyethyl)lauramide | 00 | + | 0 | 00 | — | — |
| 2. N,N-bis(2-furoyloxyethyl)lauramide | + | 0 | 0 | 00 | — | — |
| 3. N,N-bis(2-trimethylacetoxyethyl)lauramide | 0 | + | — | 00 | — | — |
| 4. N,N-bis(2-lauroyloxyethyl)benzamide | 00 | 00 | — | 00 | — | 00 |
| 5. N,N-bis(2-oleoyloxyethyl)benzamide | ++ | + | + | 00 | — | — |
| 6. N,N-bis(2-erucoyloxyethyl)benzamide | 00 | 00 | 0 | 00 | — | — |
| 7. N,N-bis(2-furoyloxyethyl)oleamide | 0 | 00 | — | 0 | — | 00 |
| 8. N,N-bis(2-trimethylacetoxyethyl)oleamide | 0 | 00 | — | + | — | 00 |
| 9. N-methyl-N-(2-benzoyloxyethyl)lauramide | 0 | 00 | 0 | 0 | — | — |
| 10. N-methyl-N-(2-furoyloxyethyl)lauramide | ++ | 00 | ++ | ++ | — | — |
| 11. N-methyl-N-(2-p-toluoyloxyethyl)lauramide | + | 00 | 0 | ++ | — | — |
| 12. N-methyl-N-(2-trimethylacetoxyethyl)lauramide | ++ | 0 | — | ++ | — | + |
| 13. N-methyl-N-(2-benzoyloxyethyl)oleamide | + | 0 | 0 | + | — | — |
| 14. N-methyl-N-(2-furoyloxyethyl)oleamide | 0 | 0 | 00 | — | 00 | — |
| 15. N-methyl-N-(2-p-toluoyloxyethyl)oleamide | + | 00 | 00 | — | 0 | — |
| 16. N-methyl-N-(2-trimethylacetoxyethyl)oleamide | 0 | 00 | — | + | — | 00 |
| 17. N-methyl-N-(2-benzoyloxyethyl)erucamide | 00 | 00 | 00 | — | 0 | — |
| 18. N-methyl-N-(2-furoyloxyethyl)erucamide | ++ | ++ | — | ++ | — | 0 |
| 19. N-methyl-N-(2-p-toluoyloxyethyl)erucamide | + | 00 | — | + | — | 00 |
| 20. N-methyl-N-(2-benzoyloxyethyl)palmitamide | + | 00 | 00 | — | 00 | — |
| 21. N-methyl-N-(2-furoyloxyethyl)palmitamide | 0 | 00 | 00 | — | 00 | — |
| 22. N-methyl-N-(2-lauroyloxyethyl)benzamide | 00 | 00 | 00 | — | 0 | — |
| 23. N-methyl-N-(2-palmitoyloxyethyl)benzamide | 00 | 00 | 00 | — | 00 | — |
| 24. N-methyl-N-(2-oleoyloxyethyl)benzamide | 00 | 00 | 00 | — | 00 | — |
| 25. N-methyl-N-(2-lauroyloxyethyl)-p-toluamide | 0 | 0 | 0 | 00 | — | — |
| 26. N-methyl-N-(2-oleoyloxyethyl)-p-toluamide | 0 | + | 00 | + | — | — |

[a]

++ equal The zone of inhibition was at least 0.5 cm beyond disc at 120 hr.
+ equal The zone of inhibition was less than 0.5 cm beyond disc at 120 hr.
0 equal Organizm exhibited slight growth on the saturated disc at 120 hr.

The following examples illustrate but do not limit the scope of this invention.

EXAMPLE 1

N,N-bis(2-benzoyloxyethyl)lauramide

Twenty-eight grams (0.2 mole) of benzoyl chloride was added dropwise to a stirred mixture of 29 gms. (0.1 mole) of N,N-bis(2-hydroxyethyl)lauramide and 20 gms. (0.25 mole) of pyridine. With the final addition of benzoyl chloride approximately 50 ml. of benzene was added and the mixture stirred for approximately 1 hr. The pyridine hydrochloride salt was filtered off and the product water washed to remove the residual pyridine. The benzene solution was dried over anhydrous sodium sulfate and eluted through an alumina column to remove free acid. The product was desolventized under reduced pressure. The product, N,N-bis(2-benzoyloxyethyl)lauramide, was characterized by the appearance of ester and amide carbonyl bands 5.73 and 6.02 microns in the infrared spectrum. The absence of the OH stretching band at 2.9 microns and acid carbonyl band at 5.84 microns indicated none of the starting products were present. Total proton count based on NMR spectral analyses was indicative of the pure compound. No bands associated with impurities were observed in the NMR spectrum.

EXAMPLE 2

N,N-bis(2-furoyloxyethyl)lauramide

N,N-bis(2-furoyloxyethyl)lauramide was prepared by the procedure of example 1 from 28 gms. (0.1 mole) of N,N-bis(2-hydroxyethyl)lauramide and 26 gms. (0.2 mole) of furoyl chloride. The structure of the final product was characterized on the basis of IR and NMR spectral analyses as described in example 1.

EXAMPLE 3

N,N-bis(2-trimethylacetoxyethyl)lauramide

N,N-bis(2-trimethylacetoxyethyl)lauramide was prepared by the procedure of example 1 from 29 gms. (0.1 mole) of N,N-bis(2-hydroxyethyl)lauramide and 24 gms. (0.2 mole) of trimethylacetyl chloride. The structure of the final product was characterized on the basis of IR and NMR spectral analyses as described in example 1.

EXAMPLE 4

N,N-bis(2-lauroyloxyethyl)benzamide

N,N-bis(2-lauroyloxyethyl)-benzamide was prepared by the procedure of example 1 from 19.5 gms. (0.1 mole) of N,N-bis(2-hydroxyethyl)benzamide and 44 gms. (0.2 mole) of lauroyl chloride. The structure of the final product was characterized on the basis of IR and NMR spectral analyses as described in example 1.

EXAMPLE 5

N,N-bis(2-oleoyloxyethyl)benzamide

N,N-bis(oleoyloxyethyl)benzamide was prepared by the procedue of example 1 from 19.5 gms. (0.1 mole) of N,N-bis(2-hydroxyethyl)benzamide and 60 gms. (0.2 mole) of oleoyl chloride. The structure of the final product was characterized on the basis of IR and NMR spectral analyses as described in example 1.

EXAMPLE 6

N,N-bis(2-erucoyloxyethyl)benzamide

N,N-bis(2-erucoyloxyethyl)benzamide was prepared by the procedure of example 1 from 19.5 gms. (0.1 mole) of N,N-bis(2-hydroxyethyl)benzamide and 71 gms. (0.2 mole) of erucoyl chloride. The structure of the final product was characterized on the basis of IR and NMR spectral analyses as described in example 1.

EXAMPLE 7

N,N-bis(2-furoyloxyethyl)oleamide

N,N-bis(2-furoyloxyethyl)oleamide was prepared by the procedure of example 1 from 37 gms. (0.1 mole) of N,N-bis(2-hydroxyethyl)oleamide and 26 gms. (0.2 mole) of furoyl chloride. The structure of the final product was characterized on the basis of IR and NMR spectral analyses as described in example 1.

EXAMPLE 8

N,N-bis(2-trimethylacetoxyethyl)oleamide

N,N-bis-trimethylacetoxyethyl)oleamide was prepared by the procedure of example 1 from 37 gms. (0.1 mole) of N,N-bis(2-hydroxyethyl)oleamide and 24 gms. (0.2 mole) of trimethylacetyl chloride. The structure of the final product was characterized on the basis of IR NMR spectral analyses as described in example 1.

EXAMPLE 9

N-methyl-N-(2-benzoyloxyethyl)lauramide

N-methyl-N-(2-benzoyloxyethyl)lauramide was prepared by the procedure of example 1 from 26 gms. (0.1 mole) of N-methyl-N-(2-hydroxyethyl)lauramide and 14 gms. (0.1 mole) of benzoyl chloride. The structure of the final product was characterized on the basis of IR and NMR spectral analyses as described in example 1.

EXAMPLE 10

N-methyl-N-(2-furoyloxyethyl)lauramide

N-methyl-N-(2-furoyloxyethyl)lauramide was prepared by the procedure of example 1 from 26 gms. (0.1 mole) of N-methyl-N-(2-hydroxyethyl)lauramide and 13 gms. (0.1 mole) of furoyl chloride. The structure of the final product was characterized on the basis of IR and NMR spectral analyses as described in example 1.

EXAMPLE 11

N-methyl-N-(2-p-toluoyloxyethyl)lauramide

N-methyl-N-(2-p-toluoyloxyetyl)lauramide was prepared by the procedure of example 1 from 26 gms. (0.1 mole) of N-methyl-N-(2-hydroxyethyl)lauramide and 15 gms. (0.1 mole) of p-toluoyl chloride. The structure of the final product was characterized on the basis of IR and NMR spectral analyses as described in example 1.

EXAMPLE 12

N-methyl-N-(trimethylacetoxyethyl)lauramide

N-methyl-N-(trimethylacetoxyethyl)lauramide was prepared by the procedure of example 1 from 26 gms. (0.1 mole) of N-methyl-N-(2-hydroxyethyl)lauramide and 12 gms. (0.1 mole) trimethylacetyl chloride. The structure of the final product was characterized on the basis of IR and NMR spectral analyses as described in example 1.

EXAMPLE 13

N-methyl-N-(2-benzoyloxyethyl)oleamide

N-methyl-N-(2-benzoyloxyethyl)oleamide was prepared by the procedure of example 1 from 34 gms. (0.1 mole) of N-methyl-N-(2-hydroxyethyl)oleamide and 14 gms. (0.1 mole) of benzoyl chloride. The structure of the final product was characterized on the basis of IR and NMR spectral analyses as described in example 1.

EXAMPLE 14

N-methyl-N-(2-furoyloxyethyl)oleamide

N-methyl-N-(2-furoyloxyethyl)oleamide was prepared by the procedure of example 1 from 34 gms. (0.1 mole) of N-methyl-N-(2-hydroxyethyl)oleaide and 13 gms. (0.1 mole) of furoyl chloride. The structure of the final product was characterized on the basis of IR and NMR spectral analyses as described in example 1.

EXAMPLE 15

N-methyl-N-(2-p-toluoyloxyethyl)oleamide

N-methyl-N-(2-p-toluoyloxyethyl)oleamide was prepared by the procedure of example 1 from 34 gms. (0.1 mole) of N-methyl-N-(2-hydroxyethyl)oleamide and 15 gms. (0.1 mole) of toluoyl chloride. The structure of the final product was characterized on the basis of IR and NMR spectral analyses as described in example 1.

EXAMPLE 16

N-methyl-N-(2-trimethylacetoxyethyl)oleamide

N-methyl-N-(2-trimethylacetoxyethyl)oleamide was prepared by the procedure of example 1 from 34 gms. (0.1 mole) of N-methyl-N-(2-hydroxyethyl)oleamide and 12 gms. (0.1 mole) trimethylacetyl chloride. The structure of the final product was characterized on the basis of IR and NMR spectral analyses as described in example 1.

EXAMPLE 17

N-methyl-N-(2-benzoyloxyethyl)erucamide

N-methyl-N-(2-benzoyloxyethyl)erucamide was prepared by the procedure of example 1 from 39.5 gms. (0.1 mole) of N-methyl-N-(2-hydroxyethyl)erucamide and 14 gms. (0.1 mole) of benzoyl chloride. The structure of the final product was characterized on the basis of IR and NMR spectral analyses as described in example 1.

EXAMPLE 18

N-methyl-N-(2-furoyloxyethyl)erucamide

N-methyl-N-(2-furoyloxyethyl)erucamide was prepared by the procedure of example 1 from 39.5 gms. (0.1 mole) of N-methyl-N-(2-hydroxyethyl)erucamide and 13 gms. (0.1 mole) of furoyl chloride. The structure of the final product was characterized on the basis of IR and NMR spectral analyses as described in example 1.

EXAMPLE 19

N-methyl-N-(2-p-toluoyloxyethyl)erucamide

N-methyl-N-(2-p-toluoyloxyethyl)erucamide was prepared by the procedure of example 1 from 39.5 gms. (0.1 mole) of N-methyl-N-(2-hydroxyethyl)-erucamide and 15 gms. (0.1 mole) of toluoyl chloride. The structure of the final product was characterized on the basis of IR and NMR spectral analyses as described in example 1.

EXAMPLE 20

N-methyl-N-(2-benzoyloxyethyl)palmitamide

N-methyl-N-(2-benzoyloxyethyl)palmitamide was prepared by the procedure of example 1 from 31 gms. (0.1 mole) of N-methyl-N-(2-hydroxyethyl)palmitamide and 14 gms. (0.1 mole) of benzoyl chloride. The structure of the final product was characterized on the basis of IR and NMR spectral analyses as described in example 1.

EXAMPLE 21

N-methyl-N-(2-furoyloxyethyl)palmitamide

N-methyl-N-(2-furoyloxyethyl)palmitamide was prepared by the procedure of example 1 from 31 gms. (0.1 mole) of N-methyl-N-(2-hydroxyethyl)palmitamide and 13 gms. (0.1 mole) of furoyl chloride. The structure of the final product was characterized on the basis of IR and NMR spectral analyses as described in example 1.

EXAMPLE 22

N-methyl-N-(2-lauroyloxyethyl)benzamide

N-methyl-N-(2-lauroyloxyethyl)benzamide was prepared by the procedure of example 1 from 18 gms. (0.1 mole) of N-methyl-(2-hydroxyethyl)benzamide and 22 gms. (0.1 mole) of lauroyl chloride. The structure of the final product was characterized on the basis of IR and NMR spectral analyses as described in example 1.

EXAMPLE 23

N-methyl-N-(2-palmitoyloxyethyl)benzamide

N-methyl-N-(2-palmitoyloxyethyl)benzamide was prepared by the procedure of example 1 from 18 gms. (0.1 mole) of N-methyl-N-(2-hydroxyethyl)benzamide and 26 gms. (0.1 mole) of palmitoyl chloride. The structure of the final product was characterized on the basis of IR and NMR spectral analyses as described in example 1.

EXAMPLE 24

N-methyl-N-(2-oleoyloxyethyl)benzamide

N-methyl-N-2-oleoyloxyethyl)benzamide was prepared by the procedure of example 1 from 18 gms. (0.1 mole) of N-methyl-N-(2-hydroxyethyl)benzamide and 30 gms. (0.1 mole) of oleoyl chloride. The structure of the final product was characterized on the basis of IR and NMR spectral analyses as described in example 1.

EXAMPLE 25

N-methyl-N-(2-lauroyloxyethyl)-p-toluamide

N-methyl-N-(2-lauroyloxyethyl)-p-toluamide was prepared by the procedure of example 1 from 19 gms. (0.1 mole) of N-methyl-N-(2-hydroxyethyl)-p-toluamide and 22 gms. (0.1 mole) of lauroyl chloride. The structure of the final product was characterized on the basis of IR and NMR spectral analyses as described in example 1.

EXAMPLE 26

N-methyl-N-(2-oleoyloxyethyl)-p-toluamide

N-methyl-N-(2-oleoyloxyethyl)-p-toluamide was prepared by the procedure of example 1 from 19 gms. (0.1 mole) of N-methyl-N-(2-hydroxyethyl)-p-toluamide and 30 gms. (0.1 mole) of oleoyl chloride. The structure of the final product was characterized on the basis of IR and NMR spectral analyses as described in example 1.

We claim:
1. N,N-bis(2-furoyloxyethyl)lauramide.
2. N,N-bis(2-furoyloxyethyl)oleamide.
3. N-methyl-N-(2-furoyloxyethyl)lauramide.
4. N-methyl-N-(2-furoyloxyethyl)oleamide.
5. N-methyl-N-(2-furoyloxyethyl)erucamide.
6. N-methylN-(2-furoyloxyethyl)palmitamide.

* * * * *